(12) United States Patent
Ledergerber

(10) Patent No.: US 7,041,127 B2
(45) Date of Patent: May 9, 2006

(54) TEXTURED AND DRUG ELUTING CORONARY ARTERY STENT

(76) Inventor: Walter J. Ledergerber, 31 Morningwood, Laguna Niguel, CA (US) 92677

( * ) Notice: Subject to any disclaimer, the term of this patent is extended or adjusted under 35 U.S.C. 154(b) by 104 days.

(21) Appl. No.: 10/698,712

(22) Filed: Oct. 31, 2003

(65) Prior Publication Data

US 2004/0116999 A1 Jun. 17, 2004

Related U.S. Application Data

(63) Continuation-in-part of application No. 10/447,453, filed on May 28, 2003.

(51) Int. Cl.
A61F 2/06 (2006.01)

(52) U.S. Cl. .................. 623/1.31; 623/1.42
(58) Field of Classification Search .............. 623/1.14, 623/1.3, 1.31–1.32, 1.42
See application file for complete search history.

(56) References Cited

U.S. PATENT DOCUMENTS

| | | | |
|---|---|---|---|
| 5,383,929 A | | 1/1995 | Ledergerber |
| 5,647,857 A | * | 7/1997 | Anderson et al. ........... 604/264 |
| 5,800,514 A | | 9/1998 | Nunez et al. |
| 6,228,116 B1 | | 5/2001 | Ledergerber |
| 6,361,780 B1 | | 3/2002 | Ley et al. |
| 6,451,050 B1 | | 9/2002 | Rudakov et al. |
| 6,547,815 B1 | | 4/2003 | Myers |
| 6,579,314 B1 | | 6/2003 | Lombardi et al. |
| 6,663,667 B1 | * | 12/2003 | Dehdashtian et al. ...... 623/1.51 |
| 6,695,833 B1 | * | 2/2004 | Frantzen ..................... 623/1.13 |
| 2002/0052649 A1 | | 5/2002 | Greenhalgh |
| 2003/0065377 A1 | | 4/2003 | Davila et al. |
| 2003/0199993 A1 | | 10/2003 | Gellman et al. |
| 2003/0204241 A1 | | 10/2003 | Dong |
| 2003/0229389 A1 | * | 12/2003 | Escano ..................... 623/1.13 |
| 2004/0044402 A1 | | 3/2004 | Jung |
| 2004/0082989 A1 | | 4/2004 | Cook et al. |
| 2004/0116945 A1 | * | 6/2004 | Sharkawy et al. .......... 606/153 |
| 2004/0117003 A1 | | 6/2004 | Quriel et al. |
| 2004/0215338 A1 | | 10/2004 | Elkins et al. |
| 2005/0010277 A1 | * | 1/2005 | Chuter ..................... 623/1.13 |

* cited by examiner

*Primary Examiner*—Suzette J-J Gherbi
(74) *Attorney, Agent, or Firm*—O'Melveny & Myers LLP

(57) ABSTRACT

The present invention provides for reinforced and drug eluting stent-grafts and related methods of implanting and manufacturing the stent-grafts. A stent-graft of the present invention may include a tubular stent, a biocompatible covering surrounding the stent, and a supporting collar coupled to the proximal end of the stent-graft. A drug agent may be applied to a textured external surface layer of the biocompatible covering, or alternatively to a space between the textured external surface layer and a smooth luminal surface layer of the biocompatible covering, and allowed to elute over time into a wall of a body lumen after the stent-graft is deployed. The collar of the stent-graft absorbs pressure exerted on the stent-graft by fluid flow within the body lumen in order to minimize potential damage to the stent-graft, and may also include barbs to further secure the stent-graft to the body lumen.

38 Claims, 11 Drawing Sheets

US 7,041,127 B2

TEXTURED AND DRUG ELUTING CORONARY ARTERY STENT

RELATED APPLICATION INFORMATION

This application is a continuation-in-part of application Ser. No. 10/447,453, filed May 28, 2003, entitled "Textured and Drug Eluting Strent-Grafts", which is incorporated herein by reference as if fully set forth herein.

FIELD OF THE INVENTION

The present invention relates generally to implantable prostheses for body lumens, and more particularly to drug eluting and textured stent-grafts and stent-grafts specially configured for disposition within body lumens.

BACKGROUND

A typical stent used in clinical practice has an expandable metal wireframe and, accordingly, contains large voids that do not necessarily contribute to either the containment or the compression of plaque. Furthermore, the expansion of the expandable wireframe of the stent may damage the body by morcellating plaque, thereby increasing the risk of plaque causing an embolism in a segment of the body lumen downstream from the stent. For example, even with the development of advanced techniques for removal of plaque at points of stenosis, there may be plaque that remains adherent to the site of stenosis. In these situations, a conventional expandable wireframe stent, due to the force of fluids coursing through the body lumen, may morcellate such residual plaque. Accordingly, there is a need for an improved stent-graft that minimizes the risk of morcellation of plaque from the body lumen.

Stents containing a drug agent have recently been proposed. For example, clinical researchers in the area of coronary artery disease have discovered the benefit of certain drug agents such as paclitaxel and sirolimus. When these drug agents are applied to a typical stent and then placed at previously stenosed regions of a patient's coronary artery, these drugs prevent or slow plaque re-deposition, and/or prevent or slow overly robust neointimal repair, both of which may contribute to restenosis of the artery at the original point of blockage. Currently, the amount of a drug agent that may be applied to a stent is limited and the rate of elution of the drug into the body lumen is rapid. The direction of the elution of the drug is also not controlled, i.e., the drug may elute towards the lumen of the stent as well as towards a body lumen wall. As a result, there is a need for an improved stent-graft that is capable of delivering drug agents towards the blood vessel wall in a controlled manner after the stent-graft is placed in the body lumen.

SUMMARY OF THE INVENTION

The present invention is directed to stent-grafts, and related methods of implantation and manufacture, that are designed for secure placement within a body lumen through the implementation of force dissipation collars on the proximal ends of the stent-grafts. The collars may include barbs to penetrate the wall of the body lumen. The stent-grafts of the present invention may further incorporate drug agents applied within or on a textured external surface layer of a biocompatible covering of the stent-graft. The drug agents on or in the biocompatible covering of the stent-graft elute gradually over time into the wall of the body lumen.

In a first aspect of the present invention, a drug eluting stent-graft is provided that has a tubular stent, a collar, a biocompatible covering surrounding the entire tubular stent/collar and a drug agent incorporated within or applied to the stent-graft. The tubular stent has a proximal end, a distal end, a lumen between the proximal and distal ends, and a peripheral wall that includes a plurality of openings. The peripheral wall is preferably an expandable structure having a contracted or collapsed state and an expanded state. The stent is preferably formed from a material that allows the stent to be placed in the contracted or the collapsed state. Suitable materials include nitinol, titanium, tantalum, niobium, and stainless steel.

The biocompatible covering surrounding the stent includes a textured external surface layer and a smooth luminal surface layer facing the lumen of the stent. In one embodiment, the biocompatible covering is formed from a separate textured external surface layer and a separate smooth luminal surface layer that are "spot welded" together. In another embodiment, the biocompatible covering is a continuous sheet or tube of biocompatible material that includes the textured external surface layer and the smooth luminal surface layer integrated thereon.

In one embodiment of the biocompatible covering, the textured external surface layer of the covering includes a plurality of villi that are oriented away from the peripheral wall of the stent and towards a wall of the body lumen within which the stent-graft is deployed. A plurality of interstices, channels, or cuts is preferably formed by the villi. Furthermore, the plurality of villi may include villi of varying lengths, heights/depth, and axial orientations. In another embodiment, the plurality of villi includes villi that are of uniform length, height/depths, and axial orientation. Instead of a plurality of villi, the textured external surface layer of the biocompatible covering may include a plurality of filaments. The filaments may be of uniform density, or the filaments may include filaments of varying density. Alternatively, the textured external surface layer of the biocompatible covering may include a plurality of individual polygonal shaped cups. Here, each of the cups has a bottom surface, raised side walls, and a plurality of filaments disposed on the bottom surface. Additionally, neighboring cups have adjacent side walls. In another embodiment, the textured external surface layer of the biocompatible covering incorporates a plurality of nested geometric cells having an intercellular space between each cell.

The biocompatible covering is preferably formed from a biocompatible material. The biocompatible materials suitable for use with the present invention are materials such as expanded polytetrafluoroethylene (ePTFE) that promote tissue in-growth into the material, and are biologically inert, non-biodegradable when implanted in the body, non-thrombogenic, lightweight, and pliable.

Preferably, there is an attachment point or sintered "spot weld" at a plurality of openings of the peripheral wall of the stent that secures the textured external surface layer of the covering to the smooth luminal surface layer of the biocompatible covering. As a result, the biocompatible covering is secured around the stent. The attachment point or "spot weld" may be a sintered "spot weld", an epoxy application, a gluing/adhesive agent application, or a combination thereof.

The drug agent that is incorporated into the stent-graft may be paclitaxel, sirolimus, an anti-metabolite drug, an antibiotic, a steroid, or another biologically active agent. As applied to the stent-graft, the drug agent may be in a freeze-dried form. Preferably, the drug agent that is applied to the stent-graft is configured to elute from the textured external surface layer and away from the smooth luminal surface layer of the biocompatible covering. In one embodiment, the drug agent is disposed within an area or space located between the textured external surface layer and the smooth luminal surface layer of the biocompatible covering. In another embodiment, the drug agent is applied to the textured external surface layer of the biocompatible covering. For example, for embodiments of the stent-graft in which the textured external surface layer includes a plurality of interstices, channels, or cuts, the drug agent may be disposed within the interstices, channels, or cuts. In embodiments of the stent-graft in which the textured external surface layer incorporates a plurality of filaments, the drug agent may be disposed on the filaments or within spaces between the filaments. Where the stent-graft includes nested geometric cells on the textured external surface layer of the biocompatible covering, the drug agent may be applied to the intercellular space between each cell of the nested geometric cells. Additionally, the drug agent may be applied under high pressure to impregnate or penetrate the biocompatible covering, and specifically the biocompatible material.

The collar of the stent-graft is coupled to the proximal end of the stent layer by layer and includes a wire structure surrounded by a biocompatible material, an atraumatic proximal end, and a distal end coupled to the proximal end of the stent. The wire structure may be spiral-wound radially in a tubular plane paraxial to the central axis of the stent. The collar may further incorporate a plurality of barbs arrayed circumferentially around the distal end of the collar. The barbs are configured to anchor the stent-graft to a wall of the body within which the stent-graft is deployed. The leading overmolded wire loop edge enhances the atraumatic character of the proximal end of the collar, and also enhances the ability of the collar to absorb and distribute any pressurized flow of fluids against the stent-graft. In one embodiment, the leading edge of the collar, being silicone elastomer molded over wire loops, is marginally larger in diameter than the diameter of the wire structure of the collar.

In a second aspect of the present invention, a stent-graft is provided that includes a tubular stent and extending proximally therefrom, a collar with a proximal end, a distal end, a lumen, and a peripheral wall having a plurality of openings, a biocompatible textured external surface layer surrounding an outer surface of the peripheral wall, a biocompatible smooth luminal surface layer surrounding an inner surface of the peripheral wall, and a collar. In one embodiment, the textured external surface layer and the smooth luminal surface layer are formed from the same, single biocompatible covering. The textured external surface layer preferably incorporates a texture such as a plurality of villi, a plurality of filaments, a plurality of polygonal shaped cups, a plurality of geometric nested cells, or any other texture that increases the surface area of the textured external surface layer. The stent of the stent-graft is formed from a material that allows the stent-graft to be transitioned between a collapsed state prior to introduction into a body lumen and an expanded state after the stent-graft is deployed. Exemplary materials include nitinol, titanium, tantalum, niobium, stainless steel, and the like.

The collar of the stent-graft includes a wire structure that is surrounded by a biocompatible material, an atraumatic proximal end, and a distal end. The distal end of the collar is coupled to or is disposed near the proximal end of the stent. The collar is configured to expand and contract in unison or in conformity with the expandable frame of the stent. In one embodiment, the wire structure of the collar includes a plurality of loops, and each loop has a proximal end and a distal end. The proximal end of each loop may be oriented perpendicular to a central axis of the lumen of the stent in order to increase the atraumatic character of the proximal end of the collar. Preferably, the distal end of each loop includes a plurality of barbs, and more preferably includes two barbs. The barbs extend radially away from the stent-graft and are configured to engage a wall of a body lumen after the stent-graft is deployed within the body lumen. The collar may also incorporate a leading edge of biocompatible material on the proximal end that extends proximally from the wire structure, and which may be marginally greater in diameter than the wire structure.

This stent-graft may also include a drug agent configured to elute into a wall of a body lumen and away from the stent-graft. In one embodiment, the drug agent is disposed on the textured external surface layer. In another embodiment, the drug agent is disposed between the textured external surface layer and the smooth luminal surface layer. Alternatively, the drug agent may be applied under high pressure. The drug agent may be freeze-dried, and may be paclitaxel, sirolimus, an anti-metabolite drug, an antibiotic, a steroid, or another bioactive agent.

In a third aspect of the present invention, a method for supporting a wall of a body lumen is provided. A stent-graft is placed into a contracted or collapsed state and then introduced into a body lumen. The stent-graft may include a tubular stent and a collar coupled to the proximal end of the stent with a biocompatible textured covering surrounding an outer surface of the stent/collar combined structure. The collar has a collapsible structure surrounded by a biocompatible material configured to expand and contract in conformity with the stent, and also includes a plurality of barbs at the distal end of the collar. A protective sheath may be placed around the stent-graft in order to place the barbs generally flat along the body of the stent-graft.

After the stent-graft is introduced into the body lumen, the stent-graft is advanced to a desired location within the body lumen. Introducing the stent-graft into the body lumen and advancing the stent-graft within the body lumen may be accomplished while using a guidewire to assist maneuvering and placing the stent-graft.

Once the stent-graft is placed at the desired location, the protective sheath, if present, is removed, and the stent-graft is transitioned into an expanded state. In the expanded state, the textured covering of the stent-graft is placed into direct contact with the wall of the body lumen. When the expandable structure of the stent of the stent-graft is formed from a shape memory material, such as, e.g., nitinol, the transitioning of the stent-graft from the contracted or collapsed state to the expanded state generally occurs automatically and without manual intervention by a user. In other embodiments in which the stent is not manufactured using a shape memory material, the stent-graft may be transitioned to the expanded state manually by using a suitable mechanical device, such as, e.g., a balloon catheter.

Additionally, the stent-graft may be engaged with the wall of the body lumen through the use of the plurality of barbs on the collar. When transitioned to the expanded state, the barbs will engage the wall of the body lumen. Also, after deployment, the stent-graft may be pushed distally in order to further engage the barbs to the wall of the body lumen.

After the stent-graft is deployed, a drug agent that is applied to the biocompatible textured surface layer is allowed to elute gradually over time into the wall of the body lumen. The elution of the drug agent occurs away from the textured surface layer of the stent-graft and towards the wall of the body lumen.

In a fourth aspect of the present invention, a method for making a stent-graft is provided. First, a sheet of biocompatible material, which may be a flat sheet or a tubular sheet, having a textured surface area is provided. The biocompatible material is placed onto a mandrel. The biocompatible material is inverted on the mandrel such that the textured surface area faces inward, i.e., towards the body of the mandrel as opposed to away from the mandrel. A tubular expansile metallic stent having a collar or proximal end, a distal end, and a peripheral wall with a plurality of openings is provided. The collar having an atraumatic proximal end, a distal end, and a plurality of barbs extending from the distal end may be welded or otherwise affixed onto the proximal end of the stent. The stent-graft is then positioned over the biocompatible material. Next, the biocompatible material is drawn or pulled distally over the peripheral wall of the stent until the textured surface layer of the biocompatible material is located over an outer surface of the peripheral wall. Additionally, a smooth luminal surface layer of the biocompatible material is preferably positioned along an inner surface of the peripheral wall of the stent.

The biocompatible material is secured to the stent through the use of a plurality of welds extending through the plurality of openings in the peripheral wall of the stent and contact-binding the textured external and internal smooth luminal surface layers of the biocompatible material. The stent-graft is then removed from the mandrel.

The method may include the step of applying a drug agent to the biocompatible material. The drug agent may, for example, be applied to the textured surface layer of the biocompatible material. Alternatively, the drug agent may be injected into a space formed between the textured surface layer and an internal, smooth luminal surface layer of the biocompatible material. The drug agent may also be applied in a high pressure environment.

These and other objects and features of the present invention will be appreciated upon consideration of the following drawings and description.

DETAILED DESCRIPTION

Figure 1A:
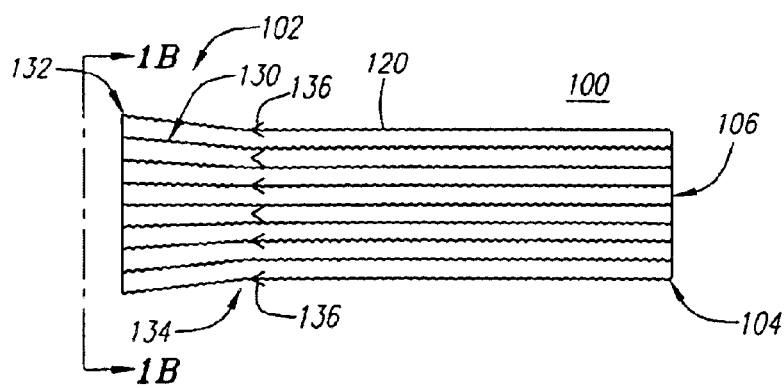
FIG. 1A is a side view of a stent-graft of the present invention.
Figure 1B:
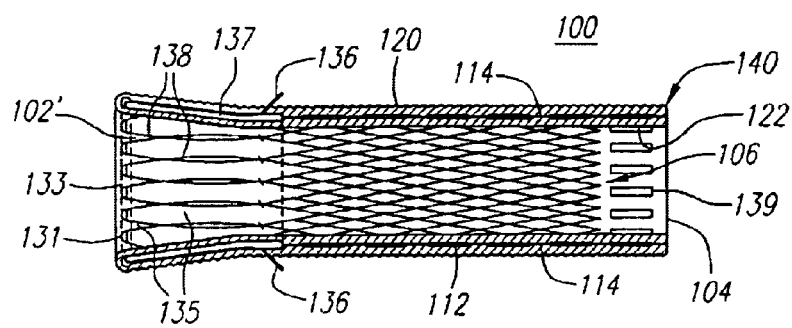
FIG. 1B is a cross-sectional side view of the stent-graft of FIG. 1A, taken along the line 1B—1B in FIG. 1A.

Turning now to the drawings, FIGS. 1A and 1B illustrate one embodiment of the stent-graft 100 of the present invention. FIG. 1A shows a side view of the stent-graft 100, and FIG. 1B shows a cross-sectional side view of the stent-graft 100 along the line 1B—1B in FIG. 1A. The stent-graft 100 includes a stent 110, which is best illustrated in FIG. 1B, a textured external surface layer 120, a smooth internal luminal surface layer 122, which is best seen in FIG. 1B, and a collar 130. The stent-graft 100 is a generally tubular device, having a proximal end 102, a distal end 104, and a lumen 106 therebetween. As referenced herein, the proximal end 102 of the stent-graft 100 is the end of the stent-graft 100 that confronts or is oriented towards the flow of fluid in a body lumen, and is the end of the stent-graft 100 that is generally nearest the user or physician while the user is positioning the stent-graft 100 in the body lumen. For example, when placed within a coronary artery, the proximal end 102 of the stent-graft 100 is the aortic or inlet end of the stent-graft 100 as it is the end of the stent-graft 100 that faces the flow of blood.

Figure 2:
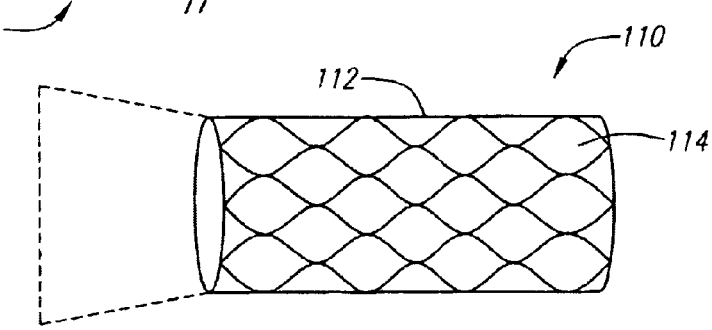
FIG. 2 shows a stent suitable for use with the stent-grafts of the present invention.

An exemplary stent 110 usable with the stent-grafts of the present invention is illustrated in isolation in FIG. 2. The stent 110 has an expandable structure 112 with a plurality of openings 114 that enables the stent 110 to be collapsed prior to insertion into a body lumen, such as, e.g., a coronary artery, aorta, and the like, and subsequently to be expanded after the stent-graft 100 is positioned at a desired location within the body lumen, such as, e.g., at a site within a coronary artery from which plaque has been removed in order to maintain arterial patency. Accordingly, the stent 110, and as a consequence the stent-graft 100, has a collapsed state and an expanded state. The expandable structure 112 defines the peripheral walls of the stent 110. The stent 110 may be formed from any suitable material that enables the stent-graft 100 to be collapsed prior to insertion and then expanded after being positioned inside a body lumen. Suitable materials include nitinol, titanium, tantalum, niobium, stainless steel, and the like. In addition, the expandable structure 112 itself may be configured in any manner that enables the stent-graft 100 to be collapsed and expanded, such as, e.g., a wireframe, a plurality of interlaced elements, a spiral coil, a wire mesh, a plurality of expandable cells, and the like. Example stents that are usable with the stent-grafts of the present invention include stents that are manufactured by MeKo (Hannover, Germany).

The stent-graft 100 further includes a biocompatible covering 140 surrounding the stent 110. The biocompatible covering 140 has a textured external surface layer 120 and a smooth luminal surface layer 122. Additionally, in one embodiment, the textured external surface layer 120 and the smooth luminal surface layer 122 are formed from the same sheet or tube of biocompatible material. FIG. 1D illustrates an embodiment of the stent-graft 100 of the present invention that has the textured external surface layer 120 and smooth luminal surface layer 122 of the biocompatible covering 140 formed from one sheet or tube, and in particular shows a cross-sectional view of the proximal end 102 of the stent-graft 100, with the collar 130 thereon, to illustrate the single sheet or tube biocompatible covering 140. In an alternative embodiment, the textured external surface layer 120 and the smooth luminal surface layer 122 are formed from different sheets or tubes of biocompatible material. In this alternative embodiment, the textured external surface layer 120 and the smooth luminal surface layer 122 are welded, epoxied, or attached by other suitable means in order to form the biocompatible covering 140. With either embodiment of the biocompatible covering 140, the biocompatible covering 140 may be secured to the stent-graft 100 by spot welds, such as, e.g., sintered spot welds, epoxy or other suitable gluing/adhesive agent applications, or otherwise affixing, the textured external surface layer 120 and the smooth luminal surface layer 122 together at the plurality of openings 114 of the stent 110.

The biocompatible covering 140, and the textured external surface layer 120 and the smooth luminal surface layer 122 thereof, is preferably formed from a material that promotes tissue in-growth into the material, has a loose structure with distracted nodes and voids between the nodes, i.e., has a mesh-like porous structure, and is biologically inert, non-biodegradable when implanted in the body, non-thrombogenic, lightweight, and pliable. One particular material that is suitable for the biocompatible covering 140 is expanded polytetrafluoroethylene (ePTFE). ePTFE is readily available, and may be marketed under the tradename GORETEX®. Because ePTFE has a mesh-like, porous structure, any tissue surrounding or in contact with ePTFE tends to grow into the porous structure, thereby enabling tissue in-growth and fixation to the body. The porous structure of ePTFE also enables drug agents to be applied and penetrate into the mesh-like structure, and then to elute over time out of the biocompatible covering 140, and particularly out of the textured external surface layer 120, and into a wall of a body lumen. Suitable ePTFE may be obtained from various manufacturers, including Zeus, Inc. (Orangeburg, S.C.).

The textured external surface layer 120 of the stent-graft 100 incorporates a textured surface that increases the surface area of the stent-graft 100 that is in contact with a wall of a body lumen. As a result of the increased surface area, the degree of tissue in-growth as between the wall of the body lumen and the stent-graft 100 is increased, and the elution into the body lumen wall of any drug agents incorporated into the stent-graft 100 is also optimized. FIGS. 3A to 3G illustrate several textured surfaces that may be used in various embodiments of the textured external surface layer 120. References made in this specification to ePTFE will also be understood to apply to any other suitable biocompatible material from which the textured external surface layer 120 may be formed.

Figure 3A:
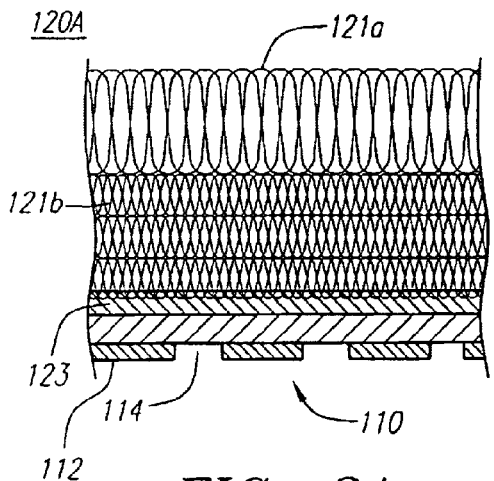
FIG. 3A shows a cross-sectional view of a textured external surface layer of a biocompatible covering of a stent-graft of the present invention, wherein the textured surface layer includes a plurality of filaments of varying density.
Figure 3B:
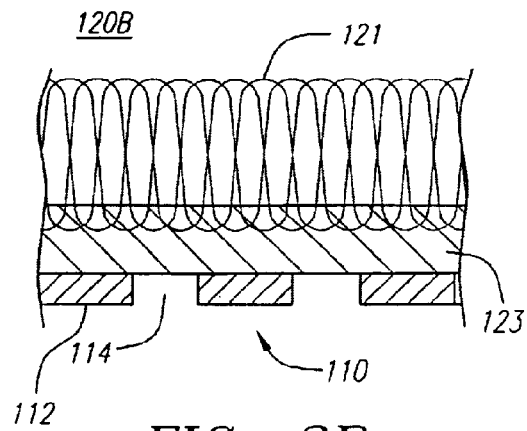
FIG. 3B shows a cross-sectional view of a textured external surface layer of a biocompatible covering of a stent-graft of the present invention, wherein the textured surface layer includes a plurality of filaments of generally the same density.

FIG. 3A shows a cross-sectional view of a textured external surface layer 120A consisting of matted long ePTFE filaments 121a, 121b. As illustrated, the filaments 121a, 121b are shown to be fused together in varying degrees and densities, with filaments 121a being more loosely fused than filaments 121b. The filaments 121a, 121b are further fused, sewn, woven, or otherwise integrated or affixed to an ePTFE sheet 123. The side of the ePTFE sheet 123 opposite the filaments 121a, 121b is coupled to the stent 110. It will be appreciated that a textured external surface layer may include ePTFE filaments that are of a generally uniform density. Such an embodiment is illustrated in FIG. 3B, which shows a cross-sectional view of a textured external surface layer 120B having ePTFE filaments 121 of generally one density affixed to an ePTFE sheet 123, which is further coupled to the stent 110.

Figure 3C:
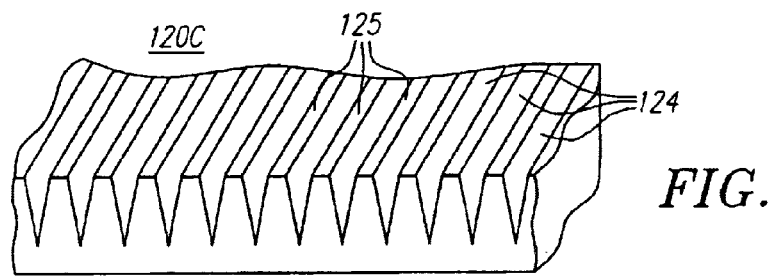
FIG. 3C shows a perspective view of a textured external surface layer of a biocompatible covering of a stent-graft of the present invention, wherein the textured surface layer includes a plurality of channels or cuts that can be abraded to form a plurality of villi.

Turning now to FIG. 3C, a perspective view of a textured external surface layer 120C is shown. Textured external surface layer 120C is manufactured from an ePTFE sheet material with a partial thickness pattern of simple cuts and/or channels 124 that can form a plurality of ridges or villi 125 of ePTFE, the villi being formed by machining of ridges to convert ridges into villi.

Figure 3D:
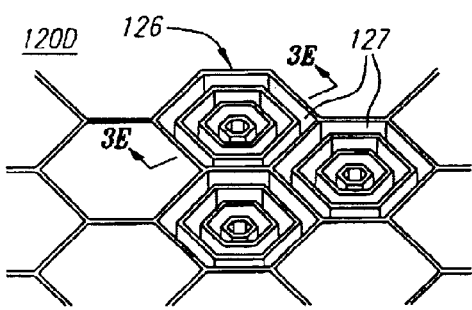
FIG. 3D shows a perspective view of a textured external surface layer of a biocompatible covering of a stent-graft of the present invention, wherein the textured surface layer includes a plurality of nested geometric cells.
Figure 3E:
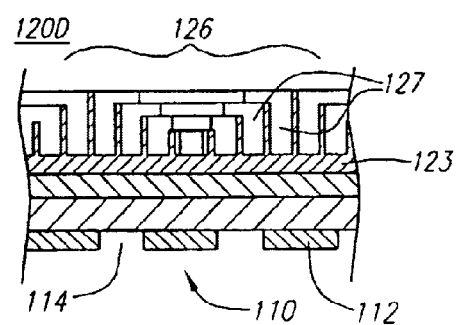
FIG. 3E shows a cross-sectional view of the textured external surface layer of FIG. 3D, taken along the line 3E—3E in FIG. 3D.

FIG. 3D illustrates a textured external surface layer 120D that includes a pattern of nested geometric cells 126 over the surface layer 120D. Although hexagonal cells are shown, it will be appreciated that other geometric patterned cells may also be utilized. FIG. 3E is a cross-sectional view of textured external surface layer 120D along the line 3E—3E in FIG. 3D. All of the nested geometric cells 126 are attached on or formed from a common ePTFE sheet 123 that is in contact with the stent 110. As seen in FIG. 3E, the geometric cells within any particular set of nested geometric cells 126 may be of varying heights. Additionally, an intercellular space 127 is located between each geometric cell.

Figure 3F:
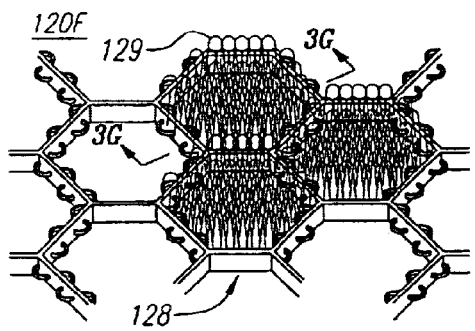
FIG. 3F shows a perspective view of a textured external surface layer of a biocompatible covering of a stent-graft of the present invention, wherein the textured surface layer includes a plurality of polygonal shaped cups.

FIG. 3F shows another embodiment of the textured external surface, namely textured external surface layer 120F.

Figure 3G:
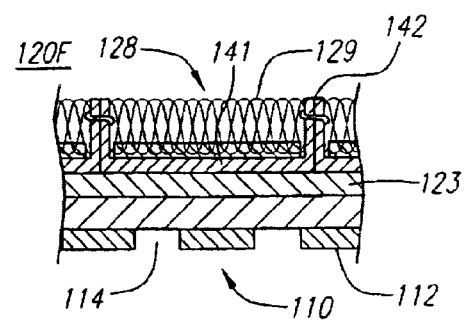
FIG. 3G shows a cross-sectional view of the textured external surface layer of FIG. 3F, taken along the line 3G—3G in FIG. 3F.

FIG. 3G is a cross-sectional view of textured external surface layer 120F taken along the line 3G—3G in FIG. 3F. Textured external surface layer 120F includes a plurality of individual polygonal shaped cups 128. Each cup 128 has a bottom surface 141, raised side walls 142, and a plurality of filaments 129 disposed on the bottom surface 141. Additionally, neighboring cups 128 have adjacent side walls 142. The cups 128, which may be formed of ePTFE, are affixed to a sheet of ePTFE 123, which is in turn placed into contact with the stent 110. Similar to textured external surface layer 120D, other geometrically-shaped cups may be utilized other than the illustrated cups 128.

Figure 3H:
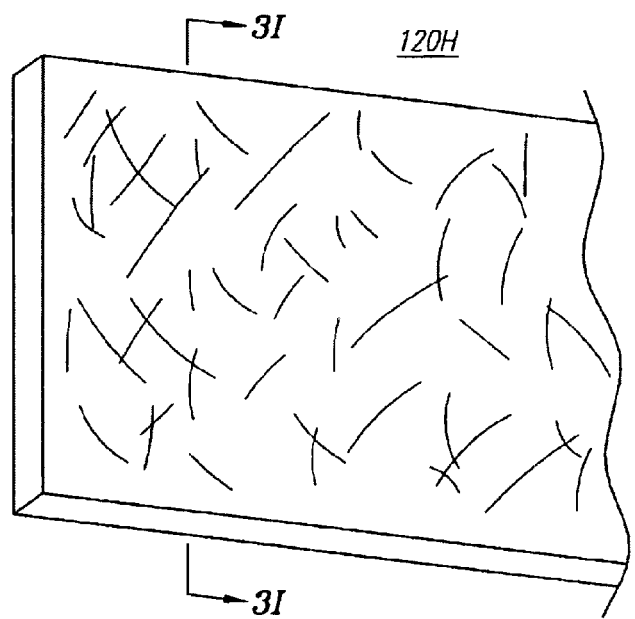
FIG. 3H shows a perspective view of a textured external surface layer of a biocompatible covering of a stent-graft of the present invention, wherein the textured surface layer includes a plurality of cuts, channels, or villi of varying depths/height, lengths, and axial orientations.
Figure 3I:
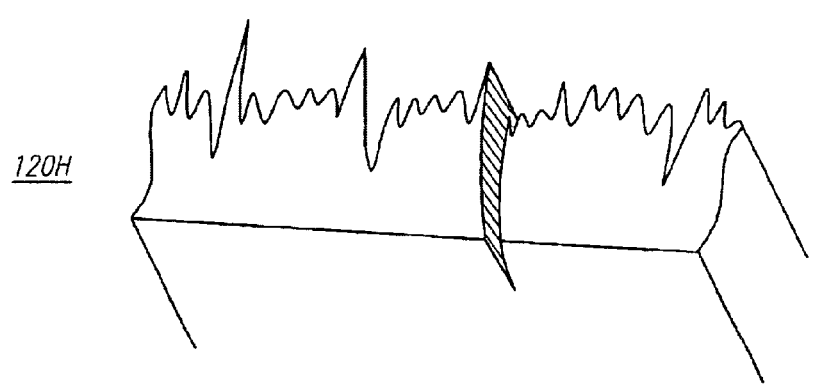
FIG. 3I shows a cross-sectional view of the textured external surface layer of FIG. 3H, taken along the line 3I—3I in FIG. 3H.

Another embodiment, textured external surface layer 120H, is illustrated in FIGS. 3H and 3I. FIG. 3H is a top-plan view of the textured external surface layer 120H, and FIG. 3I is a cross-sectional view of textured external surface layer 120H taken along the line 3I—3I. The irregular texture surface pattern may be introduced into textured external surface layer 120H by forming patterns of cuts or channels along various axes. Furthermore, the irregular pattern may include cuts and/or channels of varying depths, best seen in the cross-sectional view of FIG. 3I, as well as along different axes, which is best seen in FIG. 3H. FIG. 3I illustrates that at least some of the cuts and/or channels may extend through the bottom surface of the textured external surface layer 120H, thereby facilitating the elution of a drug agent from the textured external surface layer 120 to a body lumen wall.

U.S. Pat. No. 4,955,907, entitled "Implantable Prosthetic Device," provides additional details regarding textured coverings and particularly the use of ePTFE coverings, and is expressly incorporated by reference herein.

Drug agents may be incorporated into the stent-graft 100 by applying the drug agents onto or within the biocompatible covering 140. Example drugs suitable for incorporation into the stent-graft 100 include paclitaxel, sirolimus, antimetabolites, antibiotics, steroids, and biologically active agents. For embodiments of the stent-graft 100 having a drug agent applied to the outer or external surface thereof, the exact location to which the drug agent is applied may vary depending on the configuration of the textured external surface layer 120. For example, for textured external surface layers 120A and 120B (see FIGS. 3A and 3B, respectively), which have a plurality of filaments 121, 121a, 121b, a drug agent may be applied to the filaments 121, 121a, 121b, or may be applied to interstitial spaces formed between the filaments 121, 121a, 121b. For textured external surface layer 120C (see FIG. 3C), a drug agent may be applied to the villi 125 or to the channels 124 between the villi 125. For textured external surface layer 120D (see FIGS. 3D and 3E), the drug agent may be applied to the surfaces of the nested geometric cells 126, or to the intercellular spaces 127 between each geometric cell. For textured external surface layer 120F (see FIGS. 3F and 3G), the drug agent may be applied to any of the bottom surface 141, raised side walls 142, or plurality of filaments 129 of the polygonal shaped cups 128.

Alternatively, rather than applying the drug agent to the outer surface of the stent-graft 100, the drug agent may be injected into an area formed between the textured external surface layer 120 and the internal, smooth luminal surface layer 122 after the biocompatible covering 140 has been placed and affixed to the stent 110. In another embodiment, the stent-graft 100 includes a drug agent applied to both the textured external surface layer 120 of the stent-graft 100 and to the area formed between the textured external surface layer 120 and the internal, smooth luminal surface layer 122.

In a different embodiment, the drug agent is applied under high pressure to the biocompatible covering 140. Here, the biocompatible covering 140 may be placed within an airtight, pressurized container of the drug agent. Because the biocompatible covering 140 is preferably a material such as ePTFE that has a mesh-like, porous structure, when the covering 140 is placed into the pressurized environment, the drug agent will tend to be forced into the mesh-like structure of the covering 140 and thereby impregnate the biocompatible covering 140.

Because the biocompatible covering 140 is preferably formed from a biocompatible material such as ePTFE, which has a mesh-like configuration, any drug agent that is incorporated into the stent-graft 100 elutes gradually over time into the wall of the body lumen within which the stent-graft 100 is placed. Additionally, the application of the drug agent to the textured external surface layer 120 of the stent-graft or to an area between the textured external surface layer 120 and the internal, smooth luminal surface layer 122 of the biocompatible covering 140 allows the elution of the drug agent to flow generally away from the lumen 106 of the stent-graft 100 and towards the wall of the body lumen.

In one embodiment, the physical form of the drug agent incorporated into the stent-graft 100 is a freeze dried form. A freeze dried form of the drug agent may increase the stability of the drug agent, decrease the overall volume required for the drug agent, and increase the adherence of the drug to the stent-graft 100. Once the freeze dried drug agent is eluted into the body lumen, bodily fluids will have rehydrated and activated the drug agent.

Figure 4A:
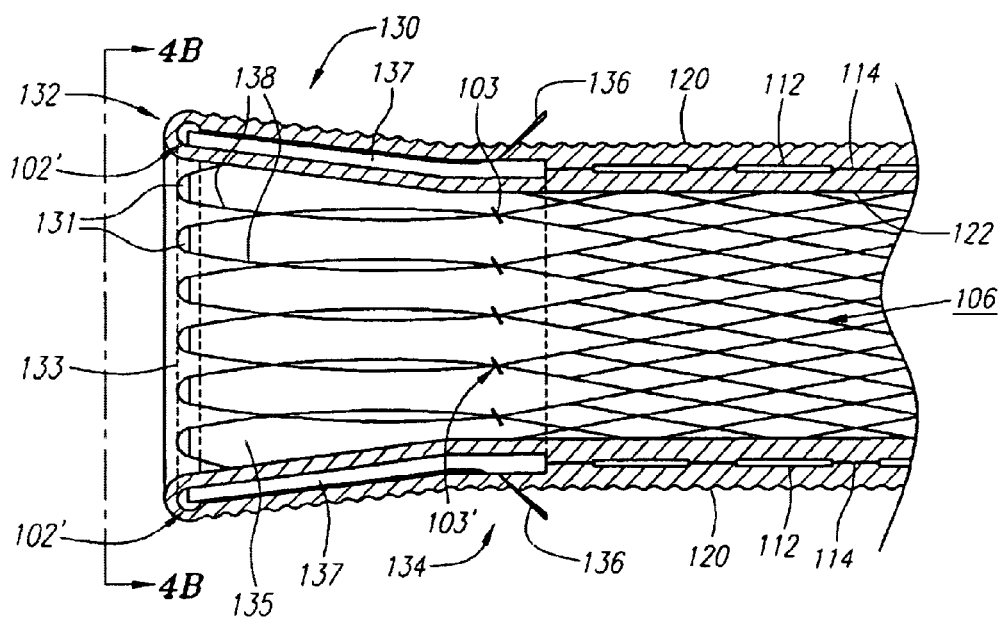
FIG. 4A is cross-sectional side view of the proximal end of the stent-graft of FIG. 1A.
Figure 4B:
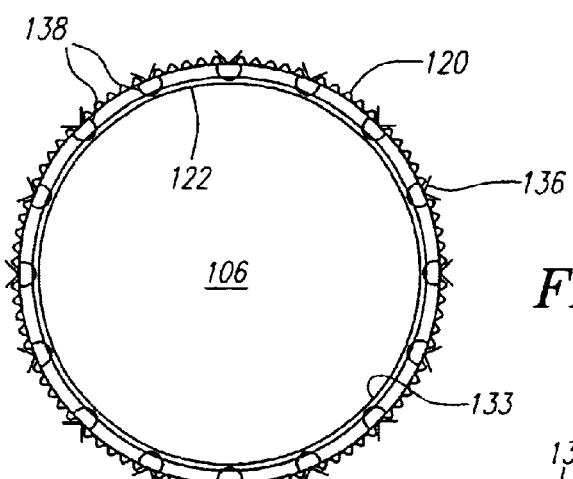
FIG. 4B is a top-plan view of the stent-graft of FIG. 4A taken along the line 4B—4B in FIG. 4A.
Figure 4C:
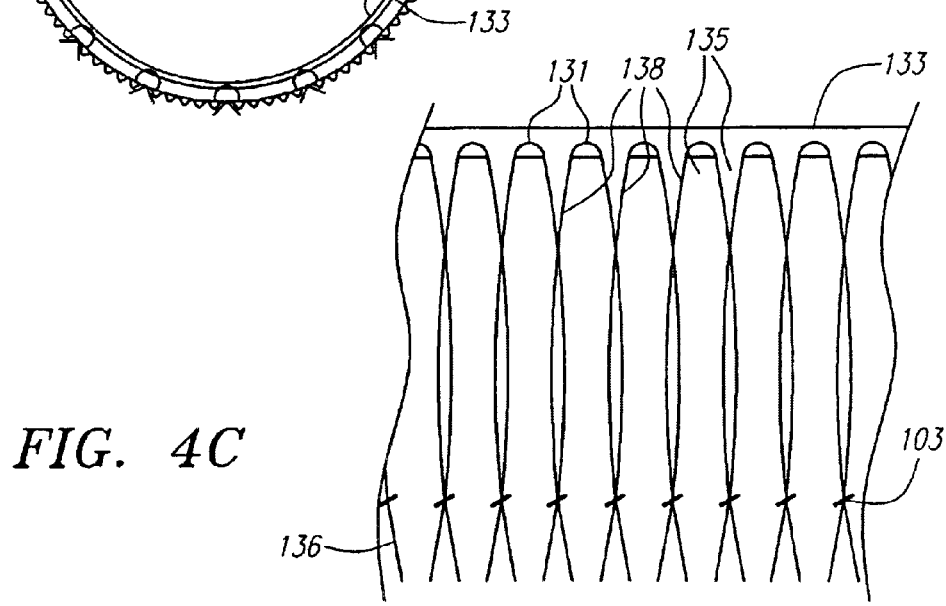
FIG. 4C is a cross-sectional side view of a collar of a stent-graft of the present invention.

As shown in FIGS. 1A and 1B, the stent-graft 100 of the present invention may include a collar 130 coupled to the proximal end 102 of the stent-graft 100. Turning now to FIGS. 4A, 4B, and 4C, an embodiment of the collar 130 of the stent-graft 100 is illustrated in further detail. FIG. 4A is a cross-sectional view of the stent-graft 100 showing the stent-graft 100 with the collar 130 coupled thereon. FIG. 4B is a cross-sectional view of the collar 130 taken along the line 4B—4B in FIG. 4A. FIG. 4C is a side view of a portion of the collar 130. The collar 130 is preferably coupled on the proximal end 103 of the stent-graft 100 in order to stabilize and support the position of the stent-graft 100 after it is placed into a body lumen. In the illustrated embodiment, the collar 130 is placed over the proximal end 103 of the stent-graft 100 such that the distal tips 103' of the proximal loops 138 are disposed on the proximal end 103 of the stent. The distal end 134 of the collar 130 is then coupled to the stent 110 at attachment points 103. The biocompatible covering 140 is disposed over and generally surrounds the collar 130. When the stent-graft 100 is placed within an artery, the collar 130 reduces the possibility of damage, i.e., tearing, of the biocompatible covering 140 by absorbing and distributing the impact of each pressure pulse of arterial blood flow at the proximal end 102 of the stent-graft 100. The collar 130 also directs fluid to flow through the lumen 106 of the stent-graft 100.

The collar 130 has a proximal end 132 and a distal end 134. The proximal end 132 of the collar 130 preferably includes a flared opening that, when the stent-graft 100 is deployed in a body lumen, presses outward towards a lumen wall to capture/shunt fluids towards the lumen 106 of the stent-graft 100, and to prevent fluid from flowing around the stent-graft 100 instead of through the lumen 106.

As previously noted, the distal end 134 of the collar 130 is coupled on the proximal end 103 of the stent-graft 100. Specifically, the collar 130 is coupled to attachment points 103, which are further illustrated with "x"s in FIG. 4C, on the proximal end of the expandable structure 112 of the stent 110. The coupling of the collar 130 to the stent 110 is performed by any suitable technique, such as, e.g., spot welding metal to metal, use of a suitable adhesive, use of metal to metal windings, or the like. The collar 130 includes an expandable wire structure 138 that is overmolded and surrounded by silicone elastomer or a similar material. The collar 130 is affixed to the stent 110, and both the stent 110 and the collar 130, which has been overmolded with silicone 137 or the like, are covered by the biocompatible covering 140 to form the stent-graft 100.

Gaps 135 are present in the expandable wire structure 138 of the collar 130 and assist in imparting an expandable quality to the collar 130. The expandable wire structure 138 of the collar 130 is configured to enable the collar 130 to expand and contract in unison or in conformity with the stent 110. The expandable wire structure 138 is capable of radially expanding, and has sufficient resilience to act similar to a spring. Accordingly, the expandable wire structure 138 of the collar 130 may be manufactured from a similar material as the expandable structure 112 of the stent 110, such as, e.g., nitinol, titanium, tantalum, niobium, stainless steel, and the like. In a preferred embodiment, the expandable wire structure 138 of the collar 130 and the expandable structure 112 of the stent 110 are formed from the same material in order to eliminate the possibility of electrolysis when the stent-graft 100 is implanted in a body lumen.

As seen in FIG. 4B, the expandable wire structure 138 of the collar 130 is preferably disposed in a tubular plane around the central axis of the stent 110. The expandable wire structure 138 is also preferably spirally wound into a plurality of loops, i.e., the expandable wire structure 138 lays in a tubular plane coaxial to the central axis of the stent 110, and the spiral winding of the structure 138 occurs in the tubular plane. In this embodiment, the collar has a substantially blunt, atraumatic proximal end 132 that is comprised of a plurality of rounded proximal ends 131 of the loops of the expandable structure 138.

The distal end 134 of each loop of the expandable structure 138 of the collar 130 includes a plurality of distally pointed barbs 136. The barbs 136 also preferably extend radially outwardly away from the stent-graft 100 when the stent-graft 100 is deployed or in the expanded state. As illustrated, the expandable wire structure 138 of the collar 130 includes two distally oriented barbs 136 for each rounded proximal end 131, as best seen in FIGS. 4A and 4C. With particular regard to FIG. 4B, it will be appreciated that the barbs 136 shown in FIG. 4B are located at the distal end 134 of the collar 130 and in the background of FIG. 4B, whereas the rounded proximal ends 131 are in the foreground of FIG. 4B and on the proximal end 132 of the collar 130. The barbs 136 are oriented to engage a wall of a body lumen and to further secure the stent-graft 100 to the lumen after the stent-graft 100 is located at a desirable position within the body lumen. For example, the barbs 136 may be oriented to point between 0° and 90° away from the body of the stent-graft 100.

In the embodiment illustrated in FIGS. 4A–4C, the rounded proximal ends 131 of the expandable wire structure 138 are oriented perpendicular to and pointed towards the central axis of the lumen 106 of the stent 110. In another embodiment, the rounded proximal ends 131 are oriented perpendicular to but pointed away from the central axis of the lumen 106. In either orientation, the atraumatic character of the proximal end 132 of the collar 130 is enhanced.

The collar 130 also preferably includes a leading edge 133 that is formed on the proximal end 132 of the collar 130, and is further preferably formed on the rounded proximal ends 131 of the expandable wire structure 138. In one embodiment, the leading edge 133 is a beaded edge formed when the wire structure 138 is overmolded with silicone elastomer, or other biocompatible material. The leading edge 133 may have a diameter that is marginally greater than the diameter of the wire structure 138 of the collar 130, as best seen in FIG. 4A.

Figure 1C:
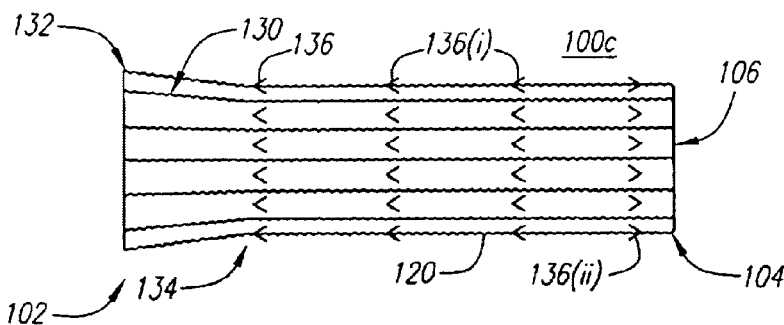
FIG. 1C shows a cross-sectional side view of a stent-graft of the present invention having a plurality of supplemental barbs along the length of the stent-graft.
Figure 1D:
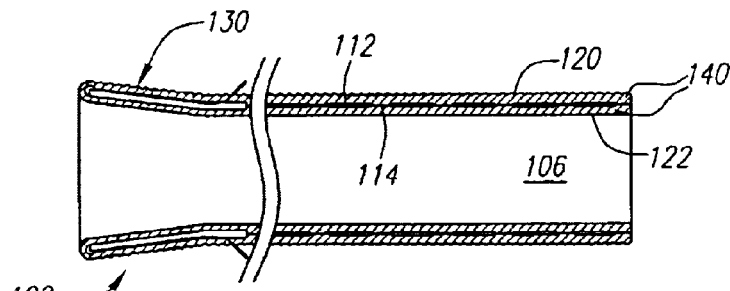
FIG. 1D shows a cross-sectional view of one form of stent-graft of the present invention having a texturized external surface layer.

Illustrated in FIG. 1C is a stent-graft 100C of the present invention that includes supplemental barbs 136(i) along the body of the stent-graft 100C. The stent-graft 100C includes at least one ring of supplemental barbs 136(i) along the length of the stent-graft 100C. As shown, the stent-graft 100C includes a plurality of rings or sets of supplemental barbs 136(i) along its length. Each set of supplemental barbs 136(i) preferably includes a ring of expandable metallic material that is the same material as the expandable structure 112 of the stent 110. Disposed on the ring are the plurality of supplemental barbs 136(i) for each set of supplemental barbs 136(i). Each supplemental set of barbs 136(i) is coupled to the expandable structure 112 of the stent 110 by spot welding the ring of each set of supplemental barbs 136(i) to the expandable structure 112 using a suitable spot welding technique, including metal to metal welding, the use of epoxy resins and gluing/adhesive agents, and the like. As with the barbs 136, the supplemental barbs 136(i) may be oriented to point between 0° and 90° from the body of the stent-graft 100.

The stent-grafts of the present invention may further include a set of opposing barbs 136(ii) that are disposed on or near the distal end 104 of the stent-grafts and are oriented to point towards the proximal end 102 of the stent-grafts. The opposing barbs 136(ii) are illustrated in FIG. 1C on stent-graft 100C. It will be appreciated, however, that any of the embodiments of the stent-grafts of the present invention, including stent-graft 100, may incorporate a set of opposing barbs 136(ii). The opposing barbs 136(ii) may be oriented to point between 0° and 90° from the body of the stent-graft 100, and point in the opposition direction as barbs 136, i.e., towards barbs 136. The opposing barbs 136(ii) aid a user in positioning the stent-graft 100 within a body lumen. The opposing barbs 136(ii) may, for example, act to initially stabilize the stent-graft 100 within the body lumen before the barbs 136 engage the lumen wall. For instance, since the opposing barbs 136(ii) are generally disposed along the distal end 104 of the stent-graft 100, the opposing barbs 136(ii) may engage a lumen wall before the barbs 136, which are located generally proximally along the stent-graft 100.

In a further embodiment of the stent-graft 100 of the present invention, the stent-graft 100 may incorporate a very very thin gold/metal foil sheet and/or a very very fine gold/metal wire or plastic screen that is sandwiched between the biocompatible covering 140 and the stent 110.

The stent-graft 100 of the present invention is suitable for placement and implantation in any body lumen in order to support the walls of the body lumen. For example, one particular use for which the stent-graft 100 is suited is to support a stenosed region of a coronary artery and to apply drug agents to the coronary artery in order to prevent plaque re-deposition and overly aggressive neointimal repair, thereby reducing the possibility of restenosis of the artery at the original blockage point. FIGS. 5A to 5D illustrate one method of implanting the stent-graft 100 in a coronary artery 10. A guidewire 20 is introduced into the body and advanced into the coronary artery 10 within the lumen AL of the artery 10 and subsequently to a stenosed region of the coronary artery 10. The distal end 22 of the guidewire 20 is preferably oriented downstream of the stenosed region, i.e., away from the aortic end or proximal (relative to the user) end 2 of the coronary artery 10.

Figure 5A:
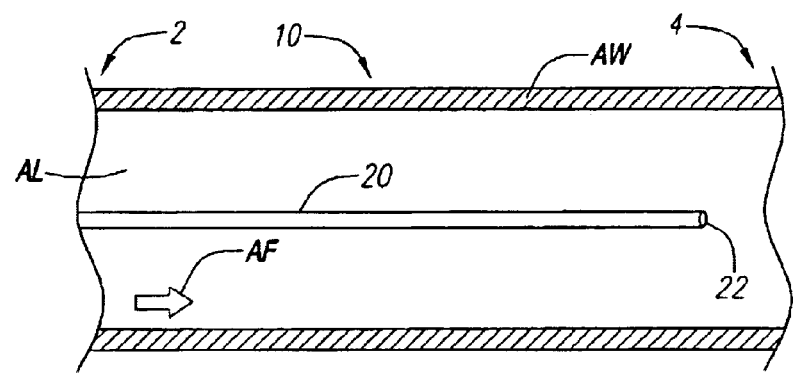
FIGS. 5A to 5D illustrate one method of implanting and deploying a stent-graft of the present invention within a body lumen.
Figure 5B:
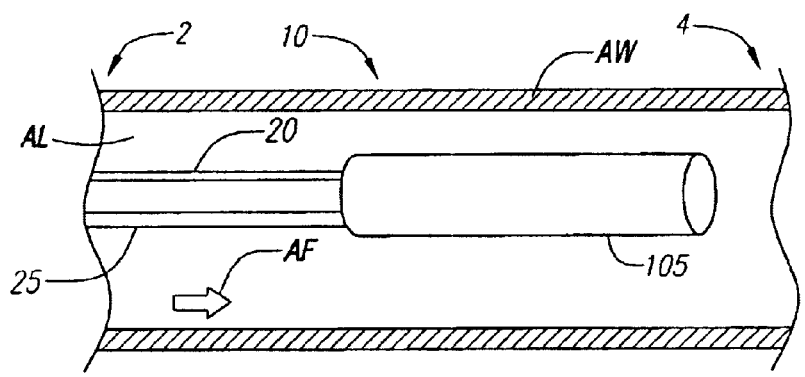
Figure 5C:
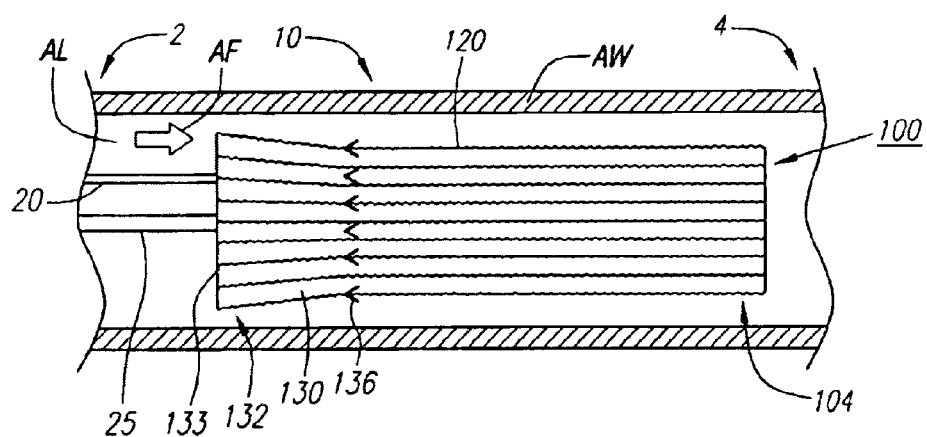

Prior to introduction into the body, the stent-graft 100 is placed into its contracted or collapsed state. In order to prevent damage to the body while the stent-graft 100, and particularly the barbs 136 of the collar 130, is being advanced within the body, a protective sheath 105 is placed over the stent-graft 100 in a proximal to distal direction. In doing so, the protective sheath 105 bends the barbs 136 towards the body of the stent-graft 100 such that the barbs 136 generally lay parallel along the stent-graft 100 and are not extending radially outward. The protective sheath 105 may be formed from plastic or any material that is suitable to maintain the barbs 136 in an orientation that is generally parallel against the body of the stent-graft 100. As shown in FIG. 5B, the protective sheath 105 extends substantially the entire length of the stent-graft 100. Alternatively, the protective sheath 105 may extend only over the collar 130 and the barbs 136, instead of the entire stent-graft 100.

The stent-graft 100 with the protective sheath 105 thereon is introduced into the body and then advanced within the lumen AL of the artery 10 along the guidewire 20 towards the stenosed region of the coronary artery 10. The stent-graft 100 may be advanced using any suitable mechanism, such as, e.g., a balloon catheter assembly 25.

Figure 5D:
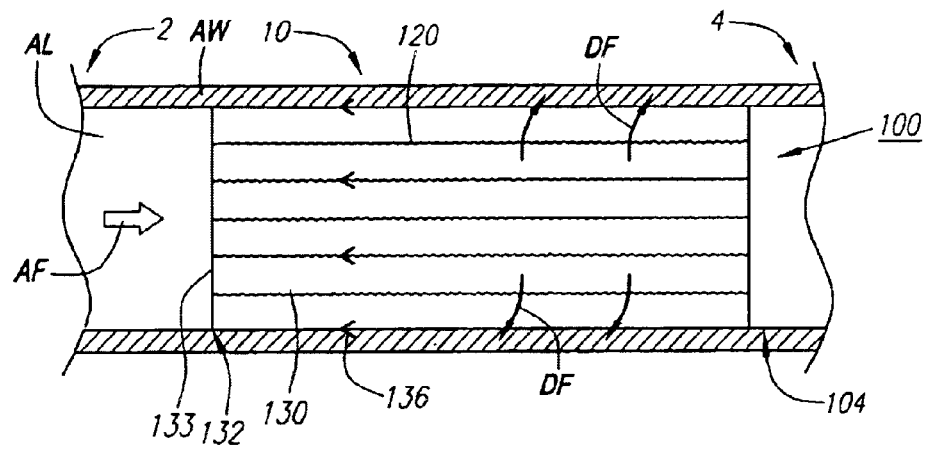
Figure 5E:
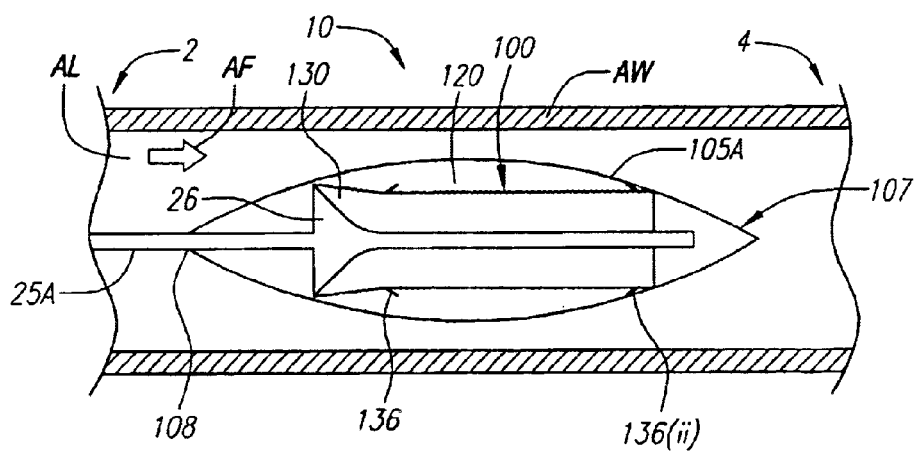
FIG. 5E illustrates the use of an elongate protective sheath with acute ends while implanting and deploying a stent-graft of the present invention.

Turning to FIG. 5E, another embodiment of a protective sheath suitable for use with the stent-grafts of the present invention, protective sheath 105A, is illustrated. FIG. 5E shows a cross-sectional view of protective sheath 105A, along with a stent-graft 100 that also includes opposing barbs 136(ii). Protective sheath 105A is elongate in shape, with a generally acute or pointed distal end 107 and a generally acute or pointed proximal end 108. The pointed distal end 106 is especially suited to reduce morcellation of plaque while the protective sheath 105A, and the stent-graft 100 therein, is being advanced positioned within a body lumen. Additionally, a specialized catheter 25A may be used to position the stent-graft 100. Catheter 25A includes a butt-end section 26 that abuts the collar 130 and increases the ability of a user to push and position the stent-graft 100 within the body.

Turning back to FIG. 5C, after the stent-graft 100 is advanced to the stenosed region, the protective sheath 105 is removed from the stent-graft 100 in order to allow the barbs 136 to deploy. The barbs 136 tend to extend radially away from the stent-graft 100 after the protective sheath 105 is removed.

Once the stent-graft 100 is placed in a desired location, the stent-graft 100 is expanded or transitioned to its expanded state. Depending on the particular embodiment of the stent-graft 100, the stent-graft 100 may automatically expand, such as, e.g., when the expandable structure 112 of the stent 110 is formed from nitinol or other shape memory alloy or material, or the stent-graft 100 may be transitioned to the expanded state using a balloon catheter 25 or other mechanical tool. As seen in FIG. 5D, when the stent-graft 100 is in its expanded state, the barbs 136 of the collar 130 of the stent-graft 100 engage the arterial walls AF of the coronary artery 10 in order to stabilize the position of the stent-graft 100 within the artery 10. Additionally, the collar 130, and the leading edge 133 of the collar 130, is oriented towards or confronting the direction of blood flow AF, thereby absorbing and distributing the pressure pulse of the arterial flow AF, and reducing the possibility of damage to the stent-graft 100. To further stabilize the stent-graft 100 to the arterial walls AF, the stent-graft 100 may be pushed distally to increase the degree of engagement between the barbs 136 and the arterial walls AF. After the stent-graft 100 is deployed, the guidewire 20 is withdrawn from the body.

Once the stent-graft 100 is implanted at the stenosed region, drug agents applied to the stent-graft 100 gradually elute from the textured external surface layer 120 and into the arterial walls AW. The direction of drug elution is illustrated by arrows DF in FIG. 5D.

The stent-graft 100 of the present invention is capable of being manufactured using various methods. The construction of the stent-graft 100 generally involves shrouding both the internal and external surfaces of the stent-graft 100 with the biocompatible covering 140, and then stabilizing and securing the covering 140 onto the expandable structure 112 of the stent 110 and also over the collar 130. As previously noted herein, the biocompatible covering 140 includes the textured external surface layer 120 and the smooth luminal surface layer 122. In one embodiment, the textured external surface layer 120 and the smooth luminal surface layer 122 are part of a single sheet, which may be flat or a tube, that forms the biocompatible covering 140, and in another embodiment the textured external surface layer 120 and the smooth luminal surface layer 122 are separate sheets that are affixed together to form the biocompatible covering 140.

Figure 6A:
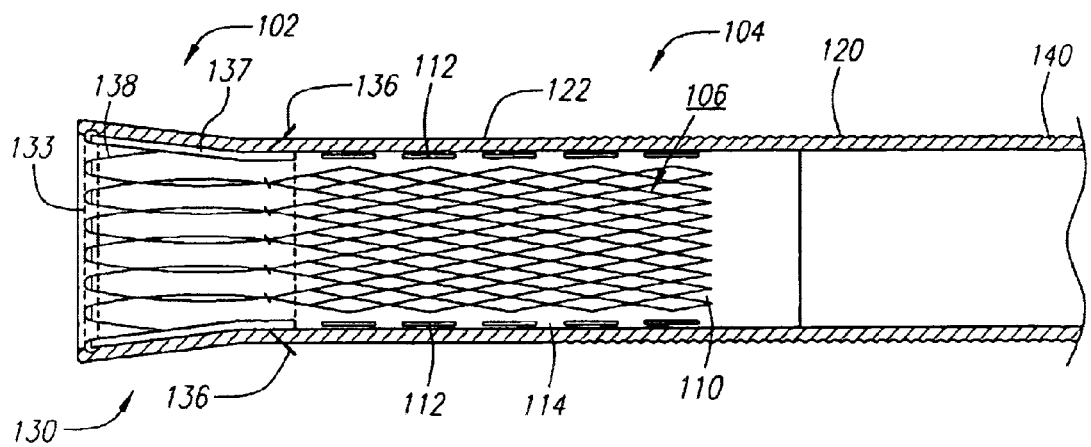
FIGS. 6A to 6D illustrate one method of manufacturing a stent-graft of the present invention.
Figure 6B:
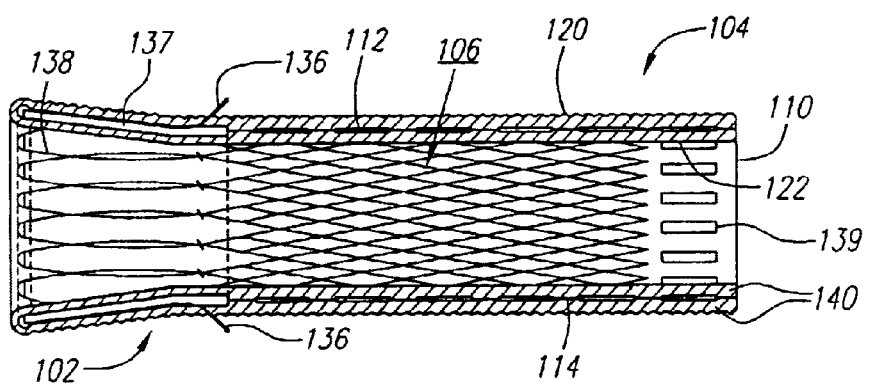
Figure 6C:
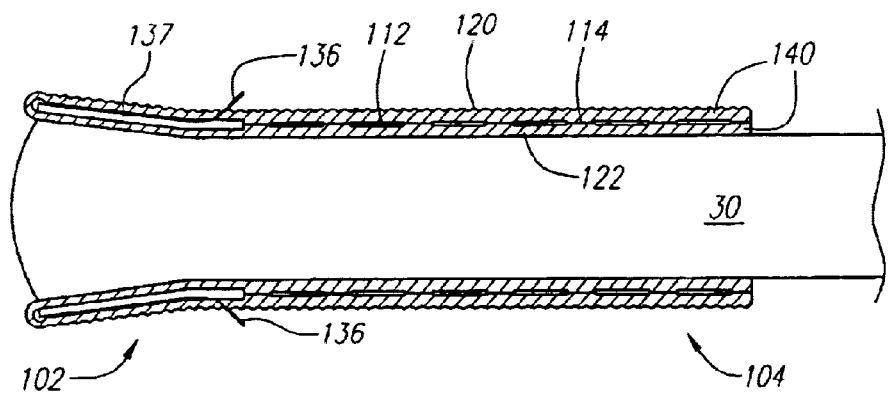
Figure 6D:
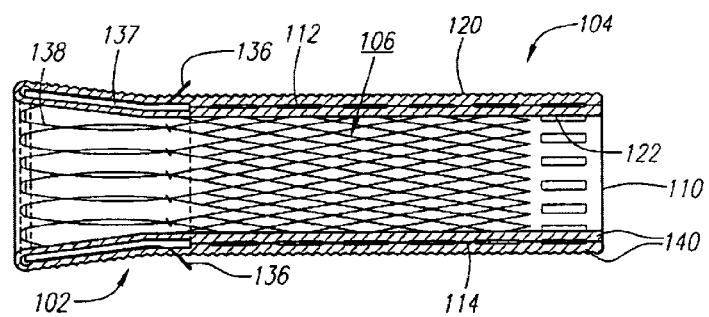

Turning now to FIGS. 6A to 6E, in one method of manufacture, a single biocompatible covering 140, with a textured external surface layer 120 and a comparatively smooth luminal surface layer 122, is stretched over an expandable structure 112 of a stent 110 that has the collar 130 coupled thereon. As seen in FIGS. 6D and 6E, which illustrate finished versions of the stent-graft 100, the collar 130 of the stent-graft 100 may be coupled to the proximal end 102 of the stent-graft 100. In one method, the collar 130 is placed over the proximal end 102 of the stent-graft 100, and then the distal end 134 of the expandable wire structure 138 of the collar 130 is affixed to the expandable structure 112 of the stent 110 using a suitable metal to metal spot welding technique.

Preferably, as best seen in FIG. 6A, the biocompatible covering 140 is at least twice the length of the stent 110, with the textured external surface layer 120 and the smooth luminal surface layer 122 portions being relatively equal in length to the stent 110. The biocompatible covering 140 may be a flat sheet of material that is wrapped around the stent 110, or the covering 140 may be a tube of material that is stretched over the stent 110.

Next, as shown in FIG. 6B, the smooth luminal surface layer 122 portion of the biocompatible covering 140 is pulled over the collar 130 and into and through the lumen 106 of the stent 110. The biocompatible covering 140 is pulled through the lumen 106 until the smooth luminal surface layer 122 portion is disposed along the internal surface of the stent 110 and the textured external surface layer 120 portion is disposed along the external surface of the stent 110. The biocompatible covering 140 is then pulled over the collar 130 portion. If a protective sleeve is present, the protective sleeve is removed. After the biocompatible covering 140 is pulled over the collar 130, the barbs 136 of the collar 130 penetrate the covering 140. Additionally, any protective sleeves covering any supplemental barbs 136(i) or opposing barbs 136(ii) that may be present are also removed in order to enable those supplemental and opposing barbs 136(i), 136(ii) to penetrate the covering 140.

Turning to FIG. 6C, the stent-graft 100 is then placed over a mandrel 30, and the biocompatible covering 140 is secured to the stent 110 by "spot welding" the textured external surface layer 120 and the smooth luminal surface layer 122 together through the plurality of openings 114 in the expandable structure 112 of the stent 110. It should be noted, however, that the biocompatible covering 140 is preferably not spot welded through gaps 135 in the expandable wire structure 138, which is overmolded with silicone or the like, of the collar 130. Suitable spot welding techniques include sintering the surface layers 120, 122 together under heated plasma pressure, and alternatively or additionally with the use of a bivalved mold, or gluing the surface layers 120, 122 together with an epoxy resin or other suitable gluing/adhesive agent. For example, when sintering the surface layers 120, 122 together, the pattern of openings 114 of the expandable structure 112 of the stent 110 to which the biocompatible covering 140 is to be sintered is indexed. An automated sintering machine may then be used to apply heat and pressure to the textured external surface layer 120 and the smooth luminal surface layer 122 portions of the biocompatible covering 140, preferably focusing on the portions of the covering 140 that overlie the openings 114 of the expandable structure 112 of the stent 110.

The degree to which the biocompatible covering 140 is secured to the stent 110, e.g., whether the fit is relatively loose or relatively tight, is controllable using various techniques. For example, one method to control the fit between the biocompatible covering 140 and the stent 110 is to vary the size of each spot weld, i.e., a smaller spot weld results in a relatively looser fit and a larger spot weld results in a relatively tighter fit. For example, having greater clearance between the spot welds and the margins of the openings 114 of the expandable structure 112 of the stent 110, i.e., having relatively smaller spot welds, results in a looser fit between the biocompatible covering 140 and the stent 110. Varying the temperature and pressure used during the sintering process also allows the degree of fit between the biocompatible covering 140 and the stent 110 to be controlled. Epoxy or other suitable gluing/adhesive agent may also be applied to the area between the surface layers 120, 122, and generally within the openings 114 of the stent 110, in order to facilitate the gluing or sintering processes.

With regard to techniques using an epoxy resin or other gluing/adhesive agent to affix the surface layers 120, 122 together, the epoxy resin or adhesive agent may be cured using any suitable technique, including the use of pressure, heat, ultraviolet light, and the like. Excess material may be trimmed from the distal end of the biocompatible covering 140, i.e., material that extends beyond the distal end of the stent 110, and the trimmed distal end of the biocompatible covering 140 may be spot welded together at 139 around the distal end of the stent 110 to form a continuous covering around the stent 110. In an alternative embodiment, a portion of the expandable structure 112 of the stent 110 is allowed to protrude from the biocompatible covering 140, either at the proximal 102 or distal 104 end of the stent-graft 100, to allow the expandable structure 112 to directly contact a wall of the body lumen.

After the biocompatible covering 140 is secured to the stent 110 and over the collar 130, a drug agent may be applied to the textured external surface layer 120 via any suitable method, such as, e.g., by spraying or painting the drug agent onto the textured external surface layer 120. The drug agent is then lyophilized, i.e., freeze dried. Alternatively, the drug agent may be injected into the space between the textured external surface layer 120 and the smooth luminal surface layer 122, or applied under high pressure. In another method of manufacture, the drug agent is applied to or injected into the biocompatible covering 140 prior to the placement of the biocompatible covering 140 over the stent 110 and collar 130. The finished stent-graft 100 is then removed from the mandrel 30.

Figure 7A:
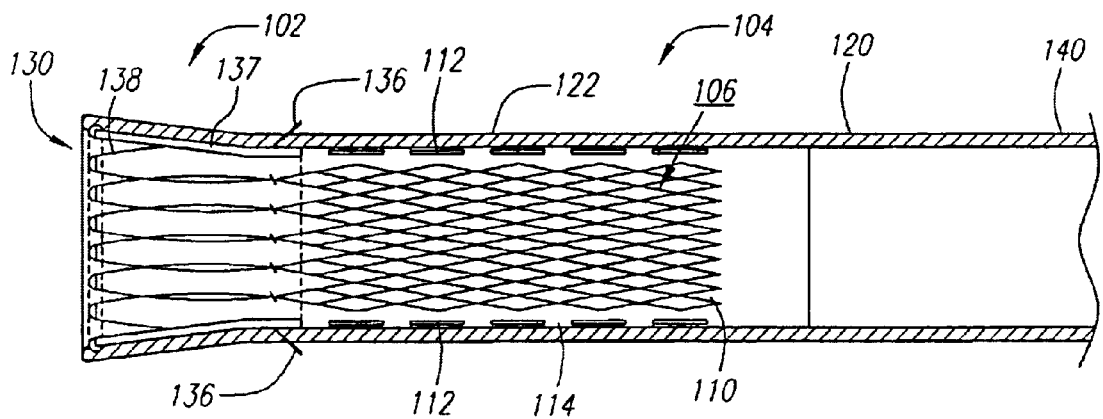
FIGS. 7A to 7C illustrate another method of manufacturing a stent-graft of the present invention.
Figure 7B:
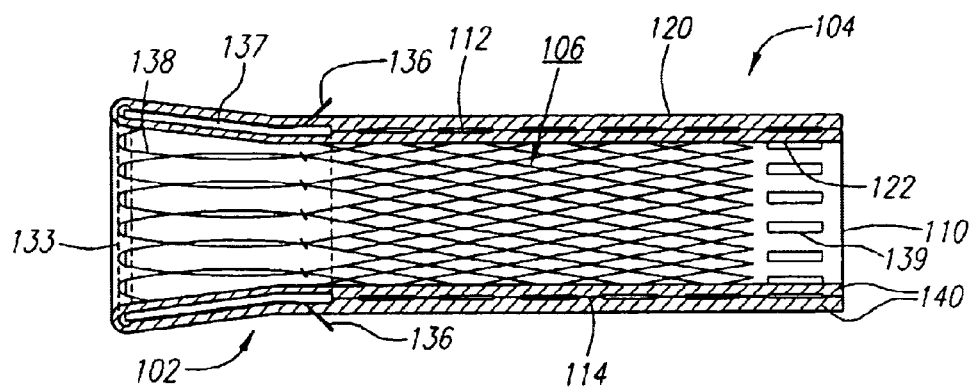
Figure 7C:
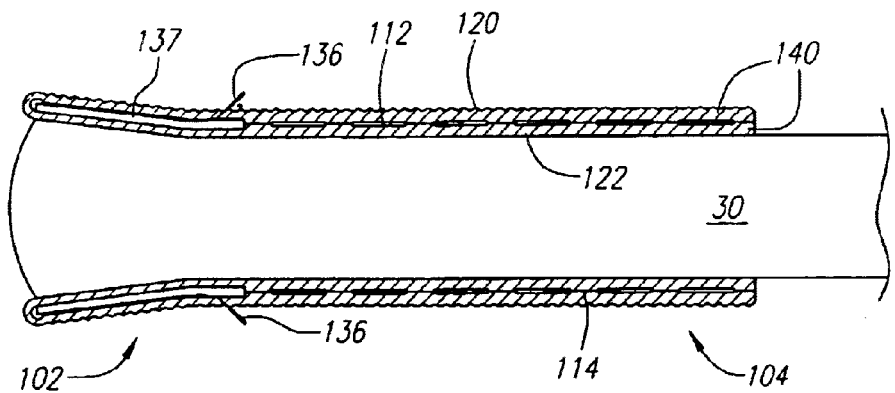

Illustrated in FIGS. 7A to 7C is another method for manufacturing the stent-graft 100 of the present invention. Here, the textured external surface layer 120 of the biocompatible covering 140 may be formed after the biocompatible covering 140 is secured to the stent 110. Turning first to FIG. 7A, a biocompatible covering 140 that is substantially smooth and preferably of uniform thickness is stretched over an expandable structure 112 of a stent 110. As illustrated, the stent 110 has coupled thereon a collar 130. The barbs 136 of the collar 130 pierce the biocompatible covering 140 after the biocompatible covering 140 is stretched over the collar 130. As with the previously described method of manufacture, protective sleeves may be used to bias the barbs 136 (and/or supplemental barbs 136(i) and opposing barbs 136(ii) if present) to lay generally parallel to the body of the stent 110 while the biocompatible covering 140 is being stretched over the collar 130, and then removed to allow the barbs 136 to pierce the covering 140. The biocompatible covering 140 is preferably at least twice the length of the stent 110, and may be a tube of material or a sheet of material that is wrapped around the stent 110.

The biocompatible covering 140 is then pulled over the collar 130 and into and through the lumen 106 of the stent 110. The biocompatible covering 140 is pulled distally within the lumen 106 until both the internal and external surfaces of the stent 110 are covered by the biocompatible covering 140, as seen in FIG. 7B "spot welds" 139 depict regions where the two sides of the material are attached together, such as by sintering.

The biocompatible covering 140 is next mounted on a mandrel 30, such as in FIG. 7C. Then, the biocompatible covering 140 is secured to the stent 110 using a suitable welding technique, such as, e.g., by sintering or by applying epoxy or other adhesive to the openings 114 of the expandable structure 112 of the stent 110, similar to what has been previously described herein. The biocompatible covering 140 also preferably overlies the collar 130 but is not sintered or spot welded to the collar 130 itself. Additionally, the distal end of the biocompatible covering 140 may be trimmed and spot welded 139 over the distal end of the stent 110 in order to form a continuous covering of biocompatible material around the stent 110 and the collar 130.

The textured external surface layer 120 is then formed on the biocompatible covering 140. The pattern of the textured external surface layer 120 may be formed using any suitable method, including by embossing the pattern onto the surface, mechanically cutting a pattern into the surface, or a combination of both. A cutting blade may be used to mechanically cut the textured pattern, and may be a simple single blade, a multiple blade, a static blade, or a rotating blade. After the textured external surface layer 120 is formed, a drug agent may be applied to the textured external surface layer 120 using any suitable method, including by spraying or painting the drug agent onto the textured external surface layer 120 or by injecting the drug agent into the biocompatible covering 140 between the textured external surface layer 120 and the smooth luminal surface layer 122. After the textured external surface layer 120 is formed, any desired drug agent is applied to the stent-graft 100. The finished stent-graft 100 is removed from the mandrel 30, and is similar in appearance to the embodiments shown in FIG. 6D and 6E, which show a stent-graft 100 having the collar 130 affixed to the external surface of the expandable 20 structure 112 and to the internal surface of the expandable structure 112 of the stent 110, respectively.

Figure 8A:
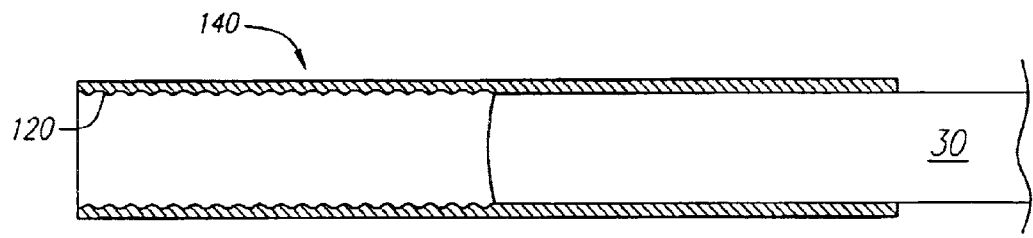
FIGS. 8A to 8E illustrate a method of manufacturing a stent-graft of the present invention in which the biocompatible covering is initially supported by a mandrel prior to being placed around and secured to the stent.

Another method of manufacture is illustrated in FIGS. 8A to 8E. First, the biocompatible covering 140 is pulled onto a mandrel 30 until approximately half of the biocompatible covering 140 is supported by the mandrel 30. Additionally, the biocompatible covering 140 is inverted on the mandrel 30 such that the textured external surface layer 120 portion of the biocompatible covering 140 is initially oriented inwardly and is not supported by the mandrel 30, as seen in FIG. 8A.

Figure 8B:
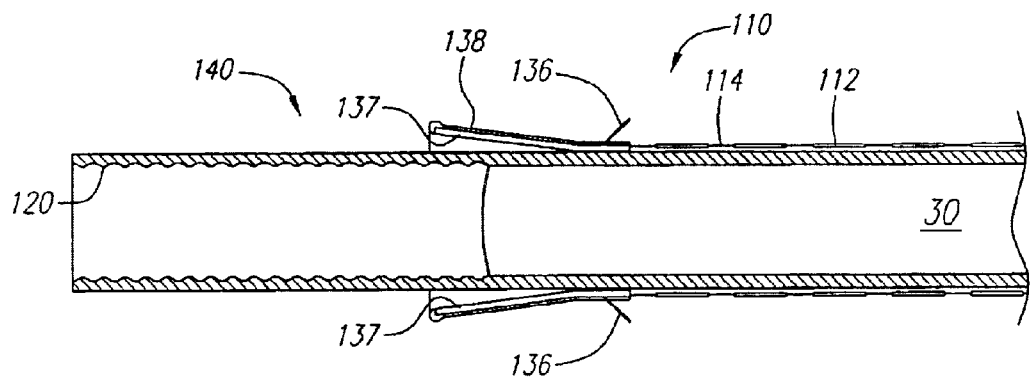

Turning to FIG. 8B, a stent 110 with a collar 130 coupled thereon is applied over the portion of the biocompatible covering 140 that is supported by the mandrel 30. Pressure is applied to the stent 110 to place the stent 110, and specifically the expandable structure 112 of the stent 110, into contact with the biocompatible covering 140.

Figure 8C:
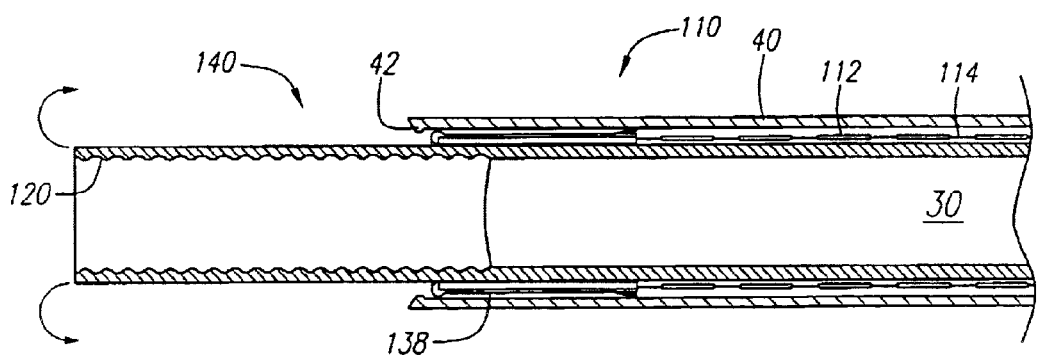

Next, as seen in FIG. 8C, an epoxy or glue/adhesive applicator assembly 40 is slipped over the stent 110. In the following discussion, references to epoxy will also be construed to include any suitable glue or adhesive agent. The epoxy/adhesive applicator assembly 40 preferably includes a TEFLON® coated metal sleeve with nozzles 42 at the proximal end, wherein the nozzles 42 are configured to apply drops of epoxy 44 to the biocompatible covering 140 at the openings 114 of the expandable structure 112 of the stent 110. The epoxy/adhesive applicator assembly 40 is designed to be retracted in a distal direction without disturbing any epoxy drops 44 that have been applied. Accordingly, the epoxy/adhesive applicator assembly 40 is preferably larger in diameter, or can be biased to be larger in diameter, than the combined diameter of the mandrel 30, biocompatible covering 140, and stent 110.

Figure 8D:
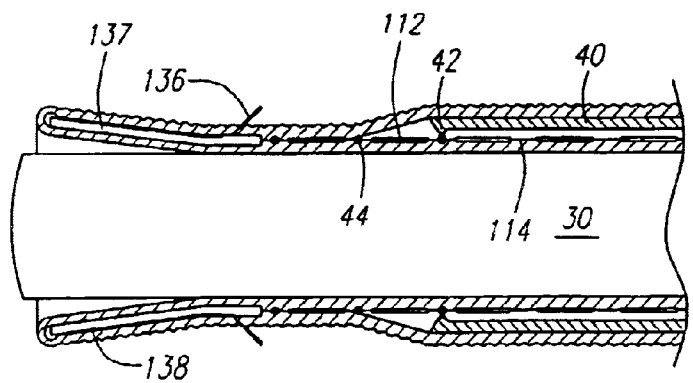

The inverted textured external surface layer 120 portion of the biocompatible covering 140 is then stretched and pulled/everted onto the external surface of the stent 110 and the collar 130. As the textured external surface layer 120 is pulled onto the external surface of the stent 110 and the collar 130, the epoxy/adhesive applicator assembly 40 is drawn distally away from the proximal end of the stent 110. While the epoxy/adhesive applicator assembly 40 is being drawn distally, the nozzles 42 of the applicator assembly 40 deposit epoxy drops 44 into the openings 114 of the expandable structure 112 of the stent 110, preferably at approximately the center of each opening 114 of the expandable structure 112. The everting of the textured external surface layer 120 portion of the biocompatible covering 140 and the withdrawal of the epoxy/adhesive applicator assembly 40 is best depicted in FIG. 8D. As with the previously described methods of manufacture, protective sleeves may be used to bias the barbs 136 of the collar 130 (and/or supplemental barbs 136(i) and opposing barbs 136(ii) if present) to lay generally parallel to the body of the stent 110 while the biocompatible covering 140 is being stretched over the collar 130, and then removed to allow the barbs 136 (and/or supplemental barbs 136(i) and opposing barbs 136(ii) if present) to pierce the covering 140.

Figure 8E:
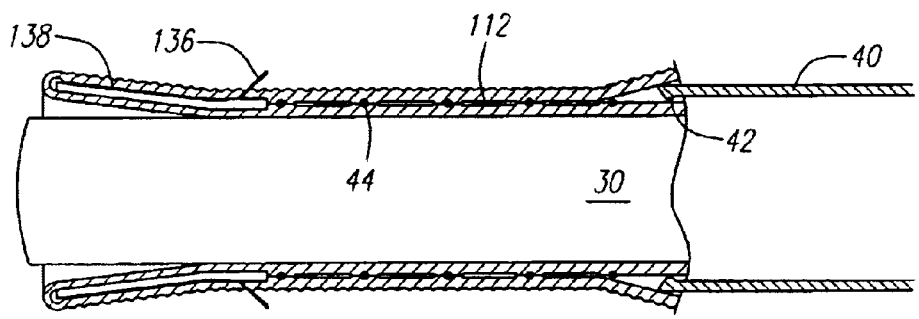

When the textured external surface layer 120 is fully drawn over the stent 110 such that the proximal end of the stent 110 is encompassed by the biocompatible covering 140, as seen in FIG. 8E, the smooth luminal surface layer 122 portion and the textured external surface layer 120 portion of the biocompatible covering 140 are forcibly joined. This is preferably accomplished using pressure applied at least above each opening 114 of the expandable structure 112 of the stent 110. Such pressure may be applied using, e.g., small pin shaped pistons to apply pressure over each opening 114 of the expandable structure 112. The pressure applied over each opening 114, and to each epoxy drop 44, assists in curing the epoxy drops 44. After the epoxy/adhesive applicator assembly 40 is fully withdrawn, the distal end of the biocompatible covering 140 is also treated with epoxy and sealed using pressure applied from a piston to seal the biocompatible covering 140 over the stent 110. To seal the distal end of the biocompatible material 140, a differently shaped piston, such as, e.g., a T-shaped piston, may be used as compared to the pins used to apply pressure over the openings 114. Subsequently, any excess material of the biocompatible covering 140 that overhangs the stent 110 is trimmed. The final product stent-graft 100 produced by this method may appear similar to the stent-graft 100 shown in FIGS. 6D or 6E.

Figure 9:
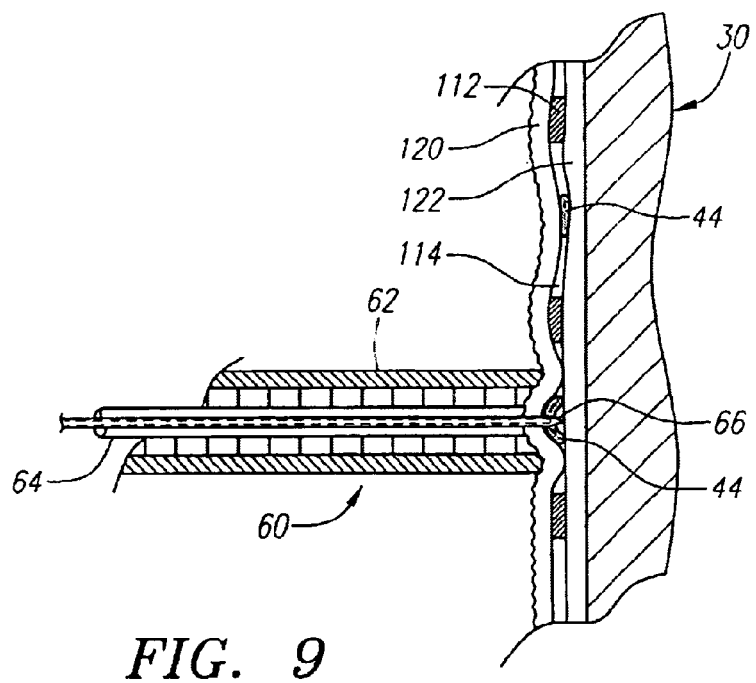
FIG. 9 illustrates a method of injecting epoxy/adhesive, or alternatively a drug agent, into a space between the textured external surface layer and smooth luminal surface layer of the biocompatible covering.

Another method of applying epoxy drops 44 between the textured external surface layer 120 and the smooth luminal surface layer 122 is illustrated in FIG. 9. Here, a needle-type applicator assembly 60 is provided that includes a hollow outer shell 62 and an injector assembly 64 disposed within the hollow outer shell 62. The hollow outer shell 62 is depressed against the textured external surface layer 120, the smooth luminal surface layer 122, and the mandrel 30 at approximately the location of an opening 114 of the expandable structure 112 of the stent 110. In this manner, the hollow outer shell 62 delimits a potential space for the application of an epoxy drop 44 between the textured external surface layer 120 and the smooth luminal surface layer 122.

The injector assembly 64 is then advanced within the hollow outer shell 62 towards the textured external surface layer 120, the smooth luminal surface layer 122, and the mandrel 30. After the injector assembly 64 contacts the textured external surface layer 120, the tip 66 of the injector assembly 64 is further advanced to penetrate the delimited potential space. A small amount of gas is then injected into the delimited potential space in order to create a real space within which an epoxy drop 44 may be injected. The injector assembly 64 is used to inject an epoxy drop 44 into the real space very rapidly following the injection of the gas. This process is repeated at each opening 114 for which a spot weld between the textured external surface layer 120 and the smooth luminal surface layer 122 is desired. The injection process may occur on multiple sides of the stent-graft 100 simultaneously.

The epoxy drops 44 applied by the needle-type applicator assembly 60 are then cured using suitable techniques, such as using pressure exerted externally through the use of small pistons, applying heat, applying ultraviolet light, and the like. It will be appreciated that the needle-type applicator assembly 60 is also suitable for injecting a drug agent into a space between the textured external surface layer 120 and the smooth luminal surface layer 122 in substantially the same manner as the application of epoxy.

In another method of manufacturing the stent-grafts of the present invention, a second external surface layer may be incorporated into a stent-graft of the present invention. Here, any of the methods of manufacture described herein are followed, except that an additional step of applying a second external layer of biocompatible material to the biocompatible material 140 is performed. The second external layer preferably does not extend in length beyond the proximal or distal ends of the stent 110, including the collar 130 when present. Additionally, the second external layer is affixed to the stent 110 in the same manner as with the biocompatible covering 140, i.e., welded to the stent 110 via sintering the second external surface layer and the biocompatible covering 140 together or by applying epoxy resin or other suitable gluing/adhesive agent to the second external surface layer and the biocompatible covering 140 and within the openings 114 of the stent 110.

Though the invention has been described with respect to specific preferred embodiments, many variations and modifications will become apparent to those skilled in the art. It is therefore the intention and expectation that the appended claims be interpreted as broadly as possible in view of the prior art in order to include all such variations and modifications.

I claim:

1. A drug eluting stent-graft, comprising:
    a tubular stent having a proximal end, a distal end, a lumen therebetween, and a peripheral wall defining the lumen, wherein the peripheral wall comprises a plurality of openings,
    a biocompatible covering surrounding the stent comprising a textured external surface layer, and a smooth luminal surface layer facing the lumen of the stent,
    a collar coupled to the proximal end of the stent, the collar comprising a wire structure surrounded by the biocompatible covering, an atraumatic proximal end, and a distal end, wherein the distal end of the collar is coupled to the proximal end of the stent, and
    a drug agent configured to elute from the textured external surface layer and away from the smooth luminal surface layer of the covering.

2. The stent-graft of claim 1, wherein the wire structure of the collar is spiral-wound radially in a tubular plane coaxial with the central axis of the stent.

3. The stent-graft of claim 1, further comprising a plurality of barbs disposed on the distal end of the collar and expandable radially outwardly to anchor the stent-graft to an interior body wall.

4. The stent-graft of claim 1, wherein the drug agent is a drug chosen from the group consisting of paclitaxel, sirolimus, an anti-metabolite drug, an antibiotic, a steroid, and a biologically active agent.

5. The stent-graft of claim 1, wherein the drug agent is disposed between the textured external surface layer and the smooth luminal surface layer of the covering.

6. The stent-grant of claim 1, wherein the biocompatible covering comprises ePTFE.

7. The stent-graft of claim 1, wherein the textured external surface layer of the covering comprises a plurality of villi oriented away from the peripheral wall of the stent.

8. The stent-graft of claim 7, wherein the plurality of villi form a plurality of interstices.

9. The stent-graft of claim 7, wherein the plurality of villi comprise villi of varying lengths.

10. The stent-graft of claim 7, wherein the plurality of villi comprise villi of uniform length.

11. The stent-graft of claim 8, wherein the drug agent is disposed within the plurality of interstices.

12. The stent-graft of claim 1, wherein the textured external surface layer of the covering comprises a plurality of filaments.

13. The stent-graft of claim 12, wherein the drug agent is disposed on the filaments.

14. The stent-graft of claim 1, wherein the textured external surface layer of the covering comprises:
    a plurality of individual polygonal shaped cups, each of the cups having a bottom surface, raised side walls, and a plurality of filaments disposed on the bottom surface, wherein neighboring cups have adjacent side walls.

15. The stent-graft of claim 14, wherein the drug agent is disposed on the filaments.

16. The stent-graft of claim 1, wherein the textured external surface layer of the covering comprises a plurality of nested geometric cells having an intercellular space between each cell.

17. The stent-graft of claim 16, wherein the drug agent is disposed within the intercellular space between each cell of the plurality of nested geometric cells.

18. The stent-graft of claim 1, wherein the smooth luminal surface layer of the covering comprises a smooth surface.

19. The stent-graft of claim 1, comprising a plurality of rings of barbs extending along the length of the stent-graft.

20. The stent-graft of claim 1, wherein the stent is formed from a material chosen from the group consisting of nitinol, titanium, tantalum, niobium, and stainless steel.

21. The stent-graft of claim 1, comprising a spot weld at a plurality of openings of the peripheral wall of the stent to secure the textured external surface layer of the covering to the smooth luminal surface layer of the covering.

22. The stent-graft of claim 21, wherein the spot weld is a spot weld chosen from the group consisting of a sintered spot weld, an epoxy application, and an adhesive agent application.

23. The stent-graft of claim 1, wherein the drug comprises a freeze-dried form of the drug.

24. The stern-graft of claim 1, wherein the covering comprises a separate textured external surface layer and a separate smooth luminal surface layer.

25. The stent-graft of claim 1, wherein the covering comprises a continuous sheet of biocompatible material having the textured external surface layer and the smooth luminal surface layer.

26. A stent-graft, comprising:
    a tubular stent having a proximal end, a distal end, a lumen therebetween, and a peripheral wall defining the lumen, wherein the peripheral wall comprises a plurality of openings,
    a biocompatible textured external surface layer surrounding an outer surface of the peripheral wall of the stent,
    a biocompatible smooth luminal surface layer surrounding an inner surface of the peripheral wall of the stent, and
    a collar having a wire structure surrounded by the biocompatible textured external surface layer and the biocompatible smooth luminal surface layer, an atraumatic proximal end, and a distal end coupled to the proximal end of the stent, wherein the collar is configured to expand and contract in conformity with the stent.

27. The stent-graft of claim 26, wherein the wire structure of the collar comprises a plurality of loops, each loop having a proximal end and a distal end.

28. The stent-graft of claim 27, wherein the proximal end of each loop is oriented perpendicular to the central axis of the lumen of the stent.

29. The stent-graft of claim 27, wherein the distal end of each loop comprises two barbs.

30. The stent-graft of claim 29, wherein the barbs extend radially away from the stent-graft, and are configured to engage a wall of a body lumen.

31. The stent-graft of claim 26, wherein the atraumatic proximal end of the collar comprises a leading edge of biocompatible material coupled to the proximal end of the collar and extending proximal from the wire structure.

32. The stent-graft of claim 31, wherein the leading edge has a diameter larger than a diameter of the wire structure.

33. The stent-graft of claim 26, further comprising a drug agent disposed on the textured external surface layer, wherein the drug is configured to elute from the textured external surface layer and away from the smooth luminal surface layer.

34. The stent-graft of claim 26, further comprising a drug agent disposed between the textured external surface layer and the smooth luminal surface layer, wherein the drug agent is configured to elute from the textured external surface layer and away from the smooth luminal surface layer.

35. The stent-graft of claim 26, further comprising a freeze-dried drug agent configured to elute from the textured external surface layer toward the body lumen wall and away from the smooth luminal surface layer, the drug agent being an agent chosen from the group consisting of paclitaxel, sirolimus, an anti-metabolite drug, an antibiotic, a steroid, and a biologically active agent.

36. The stent-graft of claim 26, wherein the textured external surface layer and the smooth luminal surface layer comprise a single biocompatible covering.

37. The stent-graft of claim 26, wherein the textured external surface layer incorporates a texture chosen from the group consisting of a plurality of villi, a plurality of filaments, a plurality of polygonal shaped cups, and a plurality of geometric nested cells.

38. The stent-graft of claim 26, wherein the stent is formed from a material chosen from the group consisting of nitinol, titanium, tantalum, niobium, and stainless steel.

\* \* \* \* \*